United States Patent
Pazenok et al.

(10) Patent No.: US 8,431,718 B2
(45) Date of Patent: Apr. 30, 2013

(54) PROCESS FOR THE PREPARATION OF 5-FLUORO-1-ALKYL-3-FLUOROALKY1-1H-PYRAZOLE-4-CARBONYL CHLORIDES AND FLUORIDES

(75) Inventors: Sergii Pazenok, Solingen (DE); Norbert Lui, Odenthal (DE); Stephanie Gary, Champagne au Mont d'Or (FR)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 13/092,429

(22) Filed: Apr. 22, 2011

(65) Prior Publication Data

US 2011/0288305 A1 Nov. 24, 2011

Related U.S. Application Data

(60) Provisional application No. 61/327,269, filed on Apr. 23, 2010.

(30) Foreign Application Priority Data

Apr. 23, 2010 (EP) .................................. 10160885

(51) Int. Cl.
*C07D 231/10* (2006.01)
(52) U.S. Cl.
USPC ..................................................... 548/374.1
(58) Field of Classification Search ............... 548/374.1
See application file for complete search history.

(56) References Cited

U.S. PATENT DOCUMENTS

| 5,480,857 | A * | 1/1996 | Cramp et al. ................. 504/239 |
| 2006/0089399 | A1 | 4/2006 | Dunkel et al. |
| 2008/0108686 | A1 | 5/2008 | Gewehr et al. |
| 2009/0306401 | A1 | 12/2009 | Neeff et al. |
| 2011/0207940 | A1 | 8/2011 | Pazenok et al. |

FOREIGN PATENT DOCUMENTS

| EP | 2 251 331 A1 | 11/2010 |
| WO | WO 2007/031212 A1 | 3/2007 |
| WO | WO 2007/087906 A1 | 8/2007 |

OTHER PUBLICATIONS

Lyga, John W. N difluoromethylation of phenylazoles. Journal of Fluorine Chemistry. 92 (1998) 141-145.*
International Search Report for International Application No. PCT/EP2011/056119, European Patent Office, Netherlands, mailed May 16, 2011.

* cited by examiner

*Primary Examiner* — Samantha Shterengarts
(74) *Attorney, Agent, or Firm* — Sterne, Kessler, Goldstein & Fox P.L.L.C.

(57) ABSTRACT

The present invention relates to a novel process for the preparation of 5-fluoro-1-alkyl-3-fluoroalkyl-1H-pyrazole-4-carbonyl halides and the intermediates occurring in this process, ethyl 5-chloro-1-methyl-3-difluoromethyl-1H-pyrazole-4-carboxylate and ethyl 5-fluoro-1-methyl-3-difluoromethyl-1H-pyrazole-4-carboxylate.

10 Claims, No Drawings

PROCESS FOR THE PREPARATION OF 5-FLUORO-1-ALKYL-3-FLUOROALKY1-1H-PYRAZOLE-4-CARBONYL CHLORIDES AND FLUORIDES

The present invention relates to a novel process for the preparation of 5-fluoro-1-alkyl-3-fluoroalkyl-1H-pyrazole-4-carbonyl halides and the intermediates occurring in this process, ethyl 5-chloro-1-methyl-3-di-fluoromethyl-1H-pyrazole-4-carboxylate and ethyl 5-fluoro-1-methyl-3-difluoromethyl-1H-pyrazole-4-carboxylate.

5-Fluoro-1-alkyl-3-fluoroalkyl-1H-pyrazole-4-carbonyl halides are important intermediates in the synthesis of plant protection agents (cf, e.g., as yet unpublished European Patent Application EP-A 2251331 and WO 2007/087906).

Pyrazolecarbonyl chlorides are usually prepared, as already described in WO 1992/012970, by reaction of carboxylic acids with a chlorinating agent. The basis of one advantage of this process is that the underlying carboxylic acids are readily accessible and are accordingly available on an industrial scale. This condition is not provided in the preparation of substituted pyrazolecarbonyl chlorides, since the corresponding substituted carboxylic acids are not readily accessible. Another process, which is described in the as yet unpublished European Patent Application 09176426 results in the acid chlorides starting from pyrazolylcarbaldehydes via a multistage synthesis.

Processes for the exchange of chlorine with fluorine (Halex processes) are known, in particular for 5-chloro-1,3-dialkyl-1H-pyrazole-4-carbonyl chlorides (cf, e.g., WO 2007/031212 and EP-A 0 776 889). In this connection, the acid chloride is converted to the acid fluoride and, in addition, the fluorination is there-by accelerated. However, if the activating group is the aldehyde (CHO) instead of the acid chloride (COCl) or the acid fluoride (COF), the reaction with potassium fluoride gives only very low yields. For example, 5-fluoro-1,3-dimethyl-1H-pyrazole-4-carbaldehyde is obtained only in 24% yield by reaction of 1,3-dimethyl-5-chloropyrazole-4-carbaldehyde with potassium fluoride (EP-A 0 776 889). A possible cause of the poor yield is also the low thermal stability of pyrazolealdhydes (cf EP-A 1 364 946).

It is accordingly the object of the present invention to make available a route for the preparation of 5-fluoro-1-alkyl-3-fluoroalkyl-1H-pyrazole-4-carbonyl halides which does not exhibit the disadvantages described in the state of the art.

The object according to the invention has now been achieved by a process for the preparation of 5-fluoro-1-alkyl-3-fluoroalkyl-1H-pyrazole-4-carbonyl halides of the formula (I)

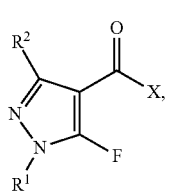

in which $R^1$ is $C_1$-$C_6$-alkyl, $R^2$ is $C_1$-$C_5$-fluoroalkyl and X is fluorine or chlorine, comprising the stages (1) chlorination of alkyl 1-alkyl-3-fluoroalkyl-1H-pyrazole-4-carboxylates of the formula (II)

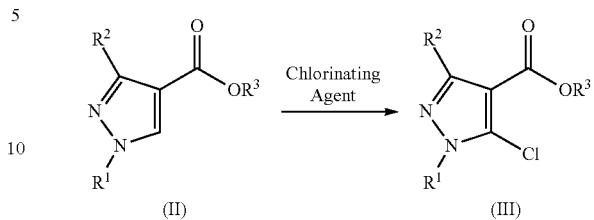

in which $R^1$ and $R^2$ have the meanings given above and $R^3$ is a linear or branched $C_{1-12}$-alkyl group, in the presence of a chlorinating agent to give alkyl 5-chloro-1-alkyl-3-fluoroalkyl-1H-pyrazole-4-carboxylates of the formula (III), in which $R^1$, $R^2$ and $R^3$ have the meanings given above;

(2a-i) fluorination of the alkyl 5-chloro-1-alkyl-3-fluoroalkyl-1H-pyrazole-4-carboxylates of the formula (III) in the presence of a fluorinating agent of the formula (IV), in which $M^+$ is $Li^+$, $Na^+$, $Cs^+$ or $Alk_4N^+$ and Alk is $C_1$-$C_4$-alkyl, to give alkyl 5-fluoro-1-alkyl-3-fluoroalkyl-1H-pyrazole-4-carboxylates of the formula (V) and (2a-ii) hydrolysis of the alkyl 5-fluoro-1-alkyl-3-fluoroalkyl-1H-pyrazole-4-carboxylates of the formula (V) to give 5-fluoro-1-alkyl-3-fluoroalkyl-1H-pyrazole-4-carboxylic acids of the formula (VIa) and (2a-iii) subsequent halogenation to give 5-fluoro-1-alkyl-3-fluoroalkyl-1H-pyrazole-4-carbonyl halides of the formula (I), in which X is fluorine or chlorine;

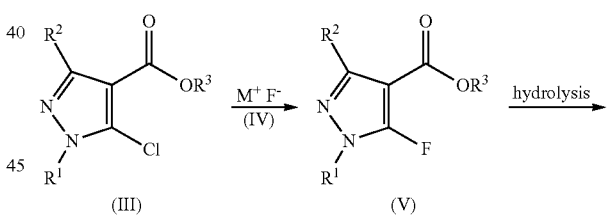

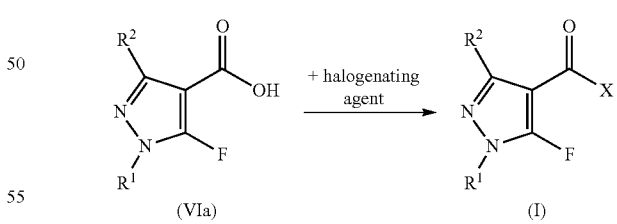

or (2b-i) hydrolysis of the alkyl 5-chloro-1-alkyl-3-fluoroalkyl-1H-pyrazole-4-carboxylates of the formula (III) to give 5-chloro-1-alkyl-3-fluoroalkyl-1H-pyrazole-4-carboxylic acids of the formula (VIb), (2b-ii) subsequent halogenation to give 5-chloro-1-alkyl-3-fluoroalkyl-1H-pyrazole-4-carbonyl halides of the formula (VII) and zole-4-carbonyl fluorides of the formula (I), in which X is fluorine.

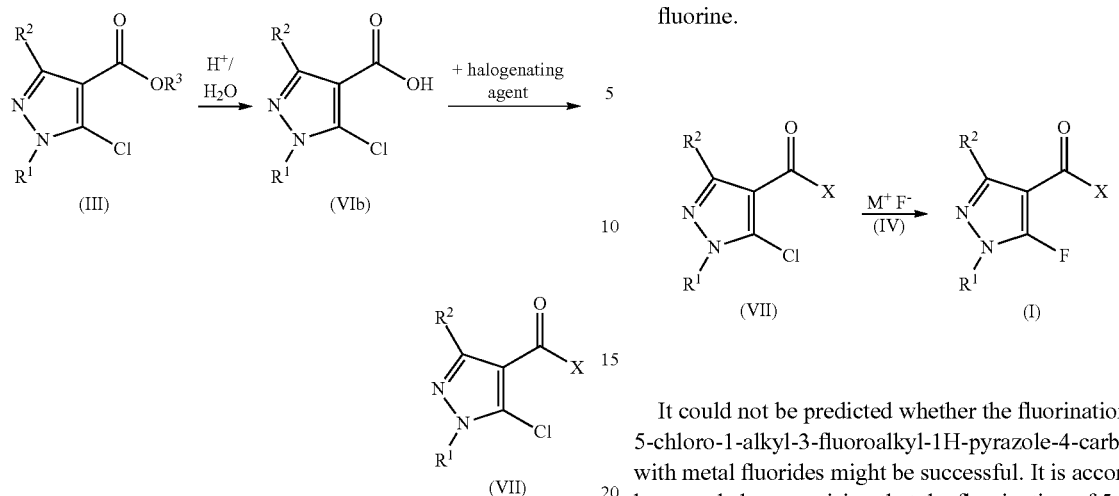

It could not be predicted whether the fluorination of alkyl 5-chloro-1-alkyl-3-fluoroalkyl-1H-pyrazole-4-carboxylates with metal fluorides might be successful. It is accordingly to be regarded as surprising that the fluorination of 5-chloro-1-alkyl-3-fluoroalkyl-1H-pyrazole-4-carboxylates with metal fluorides results, selectively and in high yield, in the novel alkyl 5-fluoro-1-alkyl-3-fluoroalkyl-1H-pyrazole-4-carboxylates.

The process according to the invention can be illustrated by the following scheme (I):

(2b-iii) fluorination of the 5-chloro-1-alkyl-3-fluoroalkyl-1H-pyrazole-4-carbonyl halides of the formula (VII) in the presence of a fluorinating agent of the formula (IV), in which $M^+$ is $Li^+$, $Na^+$, $K^+$, $Cs^+$ or $Alk_4N^+$ and Alk is $C_1$-$C_4$-alkyl, to give the 5-fluoro-1-alkyl-3-fluoroalkyl-1H-pyrazole-4-carbonyl fluorides of the formula (I), in which X is fluorine.

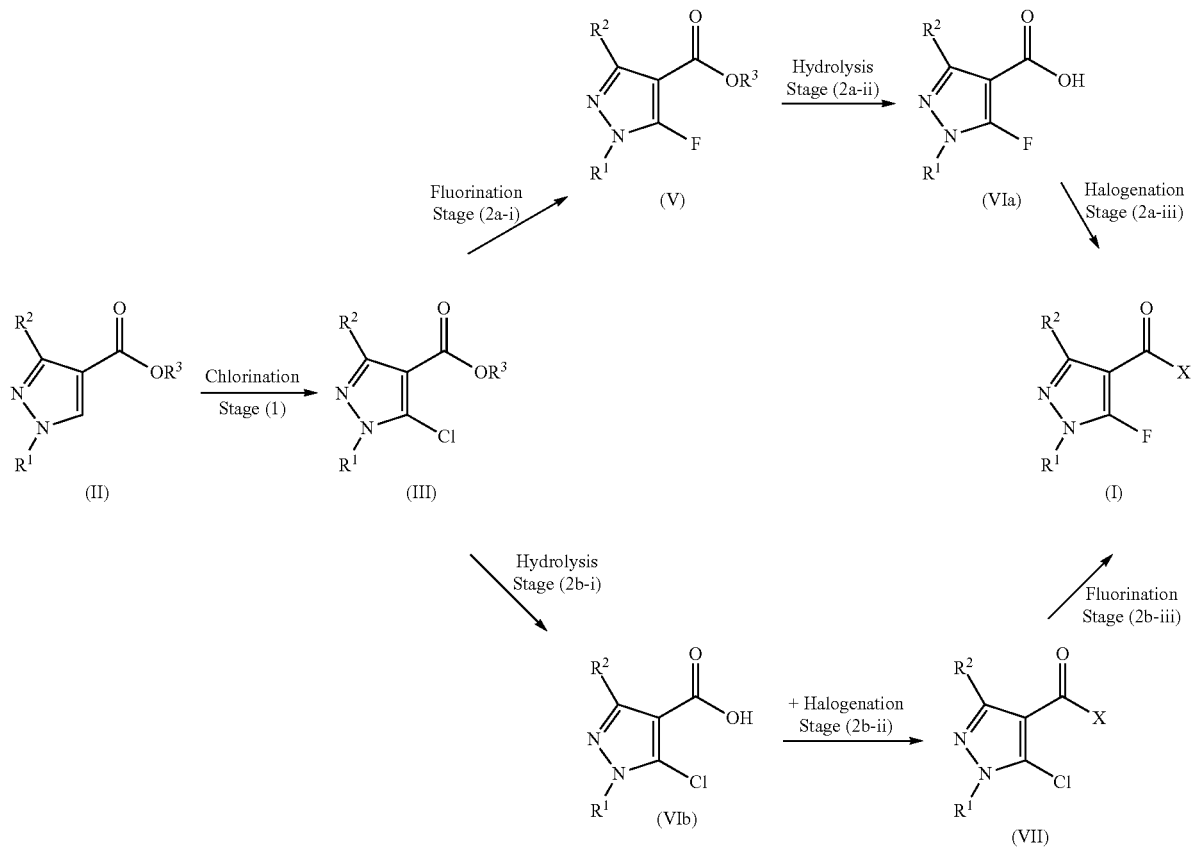

Scheme I

The alkyl 1-alkyl-3-fluoroalkyl-1H-pyrazole-4-carboxylates used as starting materials in carrying out the process according to the invention are defined generally by the formula (II). The $R^1$ and $R^3$ radicals are in this formula (II) preferably methyl, ethyl, n-propyl, isopropyl, butyl or pentyl, particularly preferably methyl, ethyl or n-propyl. The $R^2$ radical is $C_1$-$C_5$-fluoroalkyl, which is substituted with at least one fluorine atom up to perfluorination. If the fluoroalkyl is not perfluorinated, additional halogen atoms, such as chlorine and bromine, preferably chlorine, can be present as additional substituents. $R^2$ is preferably $CF_2H$, $CF_3$, $CF_2Cl$, $CCl_2F$, $C_2F_5$ or $C_3F_7$, particularly preferably $CF_2H$ and $CF_3$. Very particularly preferably, ethyl 1-methyl-3-difluoromethyl-1H-pyrazole-4-carboxylate (II-1) is used as starting material. The X group is a halogen atom chosen from fluorine and chlorine.

If the preparation of the 5-fluoro-1-alkyl-3-fluoroalkyl-1H-pyrazole-4-carbonyl halides of the formula (I) is carried out starting from the 5-fluoro-1-alkyl-3-fluoroalkyl-1H-pyrazole-4-carboxylic acids of the formula (Via), the concluding halogenation stage (2a-iii) can result either in the corresponding chloride (X=Cl) or in the fluoride (X=F), depending on the choice of the halogenating reagent.

In the alternative preparation according to the invention of the 5-fluoro-1-alkyl-3-fluoroalkyl-1H-pyrazole-4-carbonyl halides of the formula (I) by fluorination of the 5-chloro-1-alkyl-3-fluoroalkyl-1H-pyrazole-4-carbonyl halides of the formula (VII) in the presence of a fluorinating agent of the formula (IV), only 5-fluoro-1-alkyl-3-fluoroalkyl-1H-pyrazole-4-carbonyl fluorides of the formula (I) with X=F are obtained. However, these can subsequently be converted to the corresponding chlorides (X=Cl) by suitable halogen exchange reactions, for example with $SiCl_4$.

Alkyl 1-alkyl-3-polyfluoroalkyl-1H-pyrazole-4-carboxylates of the formula (II) are well known or can be prepared according to well known processes (WO 2005/23690, WO 2008/022777).

Stage 1: Chlorination

The chlorination of alkyl 1-alkyl-3-fluoroalkyl-1H-pyrazole-4-carboxylates of the formula (II) to give alkyl 5-chloro-1-alkyl-3-fluoroalkyl-1H-pyrazole-4-carboxylates of the formula (III) is carried out according to the invention in the presence of a chlorinating agent. Suitable chlorinating agents, without making any claim to be exhaustive, are, for example, $Cl_2$, $SO_2Cl_2$, $SOCl_2$, N-chlorosuccinimide or a mixture thereof. Use is preferably made, as chlorinating agent, of $Cl_2$, $SO_2Cl_2$ or a mixture thereof. $SO_2Cl_2$ is particularly preferred. The alkyl 1-alkyl-3-fluoroalkyl-1H-pyrazole-4-caroxylates of the formula (II) and the chlorinating agent are used in a molar ratio of 1:10 to 1:1, preferably of 1:5 to 1:2.

The chlorination is usually carried out at temperatures of −10 to 150° C., preferably of 20 to 100° C., and can be carried out at standard pressure or under excess pressure.

If the chlorination is carried out in the gas phase, it can optionally be carried out in the presence of an inert diluting gas, such as, e.g., nitrogen, carbon dioxide or noble gases.

The chlorination can be carried out neat or in the presence of a diluent which is inert under the prevailing reaction conditions. Use may be made, as diluents, for example, of mono- or polychlorinated aliphatic or aromatic hydrocarbons or mixtures thereof. Examples of suitable diluents are chlorobenzene, dichlorobenzenes, trichlorobenzenes, chlorotoluenes, chlorobenzotrifluorides, methylene chloride, dichloroethane, chloroform or carbon tetrachloride. Preferred diluents are chlorobenzene, 1,2-dichlorobenzene, 1,3-dichlorobenzene, 1,4-dichlorobenzene, 1,2,3-trichlorobenzene, 1,2,4-trichlorobenzene, 4-chloro-trifluoromethylbenzene, 1,3,5-trichlorobenzene, 2-chlorotoluene, 3-chlorotoluene, 4-chlorotoluene or a mixture thereof. Use is particularly preferably made of chlorobenzene.

Stages (2a-iii) and (2b-ii): Formation of the Acid Halide

The conversion of 5-chloro-1-alkyl-3-fluoroalkyl-1H-pyrazole-4-carboxylic acids of the formula (VIb) to the 5-chloro-1-alkyl-3-fluoroalkyl-1H-pyrazole-4-carbonyl chlorides of the formula (VII) or 5-fluoro-1-alkyl-3-fluoroalkyl-1H-pyrazole-4-carboxylic acids of the formula (VIa) to the 5-fluoro-1-alkyl-3-fluoroalkyl-1H-pyrazole-4-carbonyl chlorides of the formula (I), in which X=Cl, is carried out according to the invention in the presence of a chlorinating agent. Suitable chlorinating agents, without making any claim to be exhaustive, are, for example, $SOCl_2$, $COCl_2$, diphosgene, triphosgene, $POCl_3$, ClCO—COCl or a mixture thereof. Use is preferably made, as chlorinating agent, of $SOCl_2$, $COCl_2$, ClCO—COCl or a mixture thereof. $SOCl_2$ and $COCl_2$ are particularly preferred. The 5-chloro-1-alkyl-3-fluoroalkyl-1H-pyrazole-4-carboxylic acids of the formula (VIb) or the 5-fluoro-1-alkyl-3-fluoroalkyl-1H-pyrazole-4-carboxylic acids of the formula (VIa) and the chlorinating agent are used in a molar ratio of 1:5 to 1:1, preferably of 1:2 to 1:1.05.

The chlorination can be carried out neat or in the presence of a diluent which is inert under the prevailing reaction conditions. Use may be made, as diluents, for example, of mono- or polychlorinated aliphatic or aromatic hydrocarbons or mixtures thereof. Examples of suitable diluents are chlorobenzene, dichlorobenzenes, trichlorobenzenes, chlorotoluenes, chlorobenzotrifluorides, methylene chloride, dichloroethane, chloroform or carbon tetrachloride. Preferred diluents are chlorobenzene, 1,2-dichlorobenzene, 1,3-dichlorobenzene, 1,4-dichlorobenzene, 1,2,3-trichlorobenzene, 1,2,4-trichlorobenzene, 4-chloro-trifluoromethylbenzene, 1,3,5-trichlorobenzene, 2-chlorotoluene, 3-chlorotoluene, 4-chlorotoluene or a mixture thereof. Use is particularly preferably made of chlorobenzene.

The conversion of 5-chloro-1-alkyl-3-fluoroalkyl-1H-pyrazole-4-carboxylic acids of the formula (VIb) to the 5-chloro-1-alkyl-3-fluoroalkyl-1H-pyrazole-4-carbonyl fluorides of the formula (VII) or 5-fluoro-1-alkyl-3-fluoroalkyl-1H-pyrazole-4-carboxylic acids of the formula (VIa) to the 5-fluoro-1-alkyl-3-fluoroalkyl-1H-pyrazole-4-carbonyl fluorides of the formula (I), in which X=F, is carried out according to the invention in the presence of a fluorinating agent. Suitable fluorinating agents, without making any claim to be exhaustive, are, for example, $SF_4$, DAST, Deoxofluor, TFEDMA ($HCF_2$—$CF_2NMe_2$) or difluorophosgene. Use is preferably made, as fluorinating agent, of DAST or TFEDMA ($HCF_2CF_2NMe_2$). TFEDMA is particularly preferred. The 5-chloro-1-alkyl-3-fluoroalkyl-1H-pyrazole-4-carboxylic acids of the formula (VIb) or the 5-fluoro-1-alkyl-3-fluoroalkyl-1H-pyrazole-4-carboxylic acids of the formula (VIa) and the fluorinating agent are used in a molar ratio of 1:2 to 1:1, preferably of 1:2 to 1:1.5.

The fluorination can be carried out neat or in the presence of a diluent which is inert under the prevailing reaction conditions. Use may be made, as diluents, for example, of mono- or polychlorinated aliphatic or aromatic hydrocarbons or mixtures thereof. Examples of suitable diluents are chlorobenzene, dichlorobenzenes, trichlorobenzenes, chlorotoluenes, chlorobenzotrifluorides, methylene chloride, dichloroethane, chloroform or carbon tetrachloride. Preferred diluents are chlorobenzene, 1,2-dichlorobenzene, 1,3-dichlorobenzene, dichloroethane, dichloromethane or a mixture thereof. Use is particularly preferably made of chlorobenzene and dichloromethane.

Stage (2a-i) or (2b-iii): Fluorination

The fluorination of the alkyl 5-chloro-1-alkyl-3-fluoroalkyl-1H-pyrazole carboxylates of the formula (III) to give alkyl 5-fluoro-1-alkyl-3-fluoroalkyl-1H-pyrazole-4-carboxylates of the formula (V), according to stage (2a-i), is carried out according to the invention in the presence of a fluorinating agent of the formula (IV).

In an alternative embodiment of the process according to the invention, which is represented in the above Scheme I as stage (2b-iii), the 5-chloro-1-alkyl-3-fluoroalkyl-1H-pyrazole-4-carbonyl halides of the formula (VII) are finally reacted in the presence of a fluorinating agent of the formula (IV) to give the 5-fluoro-1-alkyl-3-fluoroalkyl-1H-pyrazole-4-carbonyl halides of the formula (I).

In formula (IV), M is an alkali metal cation or an ammonium cation, preferably $Li^+$, $Na^+$, $K^+$, $Cs^+$, $Alk_4N^+$ or a mixture thereof, Alk being $C_1$-$C_4$-alkyl. Use is particularly preferably made, as fluorinating agents, of sodium fluoride and potassium fluoride or a mixture thereof.

Sodium fluorine and potassium fluoride are well known chemicals for synthesis and are commercially available.

The reaction temperatures can be varied within a relatively wide range in carrying out the fluorination stage according to the invention. Generally, the operation is carried out at temperatures of 120° C. to 200° C., preferably at temperatures of 110° C. to 180° C.

The reaction time can, depending on the reactivity of the starting materials, be up to 10 hours, it being possible for the reaction to be terminated with complete conversion even earlier. Reaction times of 3-5 hours are preferred.

Use is generally made, in carrying out the process according to the invention, of between 0.8 and 1.8 mol, preferably between 1 and 1.5 mol, of fluorinating agents of the formula (IV) per exchangeable chorine atom in alkyl 5-chloro-1-alkyl-3-fluoroalkyl-1H-pyrazole-4-carboxylates of the formula (III) or in 5-chloro-1-alkyl-3-fluoroalkyl-1H-pyrazole-4-carbonyl halides of the formula (VII).

The reaction can be carried out neat or in the presence of a solvent. Suitable solvents are sulfolane, dimethyl sulphoxide (DMSO), dimethylacetamide, dimethylformamide (DMF), N-methylpyrrolidone (NMP), 1,3-dimethylimidazolinone, dichloromethane, chloroform, dichloroethane, trichloroethane, ketones, such as ace-tone, butanone, methyl isobutyl ketone or cyclohexanone, nitriles, such as acetonitrile, propionitrile, n-butyronitrile or isobutyronitrile, or hexamethylphosphoramide. Use is particularly preferably made of sulfolane, DMSO, dimethylacetamide, DMF or NMP.

The fluorination can be accelerated by addition of phase transfer catalysts.

Quaternary ammonium or phosphonium compounds or amidophosphonium salts are particularly suitable as phase transfer catalysts in carrying out the process according to the invention. Mention may be made, by way of example, of compounds such as tetramethylammonium chloride or bromide, tetrabutylammonium chloride, trimethylbenzylammonium chloride, tetrabutylammonium bromide, tetrabutylphosphonium chloride, tetrabutylphosphonium bromide, tetraphenylphosphonium chloride, tetraphenylphosphonium bromide, tetrakis(dimethylamino)phosphonium chloride or bromide, tetrakis(diethylamino)phosphonium chloride or bromide, tris(diethylamino)(dimethylamino)phosphonium chloride or bromide, tris(dimethylamino)(di-hexylamino) phosphonium chloride or bromide, tris(diethylamino)(di-hexylamino)phosphonium chloride or bromide, hexaalkylguanidinium salts or polyethylene glycol dimethyl ethers with chain lengths r of 6 to 17 and an average molar mass of 500 g/mol.

In the alternative embodiment of the process according to the invention represented in the above Scheme I as stage (2b-iii), the 5-chloro-1-alkyl-3-fluoroalkyl-1H-pyrazole-4-carbonyl halides of the formula (VII) are finally reacted in the presence of a fluorinating agent of the formula (IV) to give the 5-fluoro-1-alkyl-3-fluoroalkyl-1H-pyrazole-4-carbonyl halides of the formula (I). In this case, the halogenation stage (2b-ii) is preferably a chlorination (X=Cl) and the 5-chloro-1-alkyl-3-fluoroalkyl-1H-pyrazole-4-carbonyl chlorides of the formula (VII) obtained from this are converted, in the presence of a fluorinating agent of the formula (IV), to the 5-fluoro-1-alkyl-3-fluoroalkyl-1H-pyrazole-4-carbonyl fluorides of the formula (I) with X=F.

Both the alkyl 5-fluoro-1-alkyl-3-fluoroalkyl-1H-pyrazole-4-carboxylates of the formula (V) and the 5-fluoro-1-alkyl-3-fluoroalkyl-1H-pyrazole-4-carboxylic acids of the formula (VIa) and (VIb) are important intermediates in the synthesis of plant protection agents (cf, e.g., European Patent Application No. EP-A 2251331 and WO 2007/087906).

Stage (2b-i) and (2a-ii): Hydrolysis

The hydrolysis of the alkyl 5-chloro-1-alkyl-3-fluoroalkyl-1H-pyrazole-4-carboxylates of the formula (III) or 5-fluoro-1-alkyl-3-fluoroalkyl-1H-pyrazole-4-carboxylates of the formula (V) and the preparation of the 5-chloro-1-alkyl-3-fluoroalkyl-1H-pyrazole-4-carboxylic acids of the formula (VIb) or 5-chloro-1-alkyl-3-fluoroalkyl-1H-pyrazole-4-carboxylic acids of the formula (VIa) and the subsequent chlorination to give the 5-chloro-1-alkyl-3-fluoroalkyl-1H-pyrazole-4-carbonyl chlorides of the formula (VII), in which X=Cl, or to give the 5-fluoro-1-alkyl-3-fluoroalkyl-1H-pyrazole-4-carbonyl chlorides of the formula (I) are carried out as described in WO 2005/123690.

In a preferred embodiment of the present invention, the stages described above can be carried out without interim isolation of the intermediates produced.

An additional subject matter of the present invention is the intermediates ethyl 5-chloro-1-methyl-3-difluoromethyl-1H-pyrazole-4-carboxylate (III-1) and ethyl 5-fluoro-1-methyl-3-difluoromethyl-1H-pyrazole-4-carboxylate (V-1) produced in the process, which are passed through in the reaction of ethyl 1-methyl-3-difluoromethyl-1H-pyrazole-4-carboxylate according to the process according to the invention.

The preparation according to the invention of 5-fluoro-1, 3-diallyl-1H-pyrazole-4-carbonyl fluorides of the formula (I) is described in the following examples, in which the above description is further illustrated. However, the examples are not to be interpreted in a limiting way.

PREPARATION EXAMPLES

Example 1

Ethyl 5-chloro-1-methyl-3-difluoromethyl-1H-pyrazole-4-carboxylate (III-1)

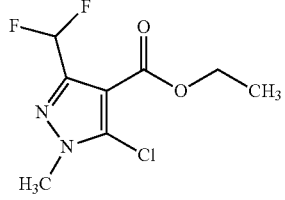

20.25 g (100 mmol) of ethyl 1-methyl-3-difluoromethyl-1H-pyrazole-4-carboxylate and 40 ml of SO$_2$Cl$_2$ are placed under argon and the mixture is heated to 60° C. and stirred at this temperature for 8 hours. After diluting the mixture with ethyl acetate, washing with water and removing the solvent under vacuum, 21 g of the product are obtained with an HPLC purity of 94%. M.p. 37-39° C.

$^1$H NMR (CDCl$_3$): δ=7.1 (1H, t), 4.3 (q, 2H), 3.9 (s, 3H), 1.4 (t, 3H) ppm.

$^{19}$F NMR (CD$_3$CN): δ=−114.9 (2F, t) ppm.

Example 2

Ethyl 5-fluoro-1-methyl-3-difluoromethyl-1H-pyrazole-4-carboxylate

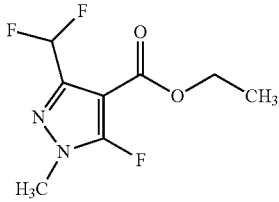

(V-1)

9.63 g (166 mmol) of spray-dried potassium fluoride, 23.8 g (100 mmol) of ethyl 5-chloro-1-methyl-3-difluoromethyl-1H-pyrazole-4-carboxylate (II-1) and 150 ml of sulpholane are heated to 190° C. with rapid stirring. The reaction is completed after 8 hours (GC monitoring). The reaction mixture is cooled down to ambient temperature, water is added to a total volume of 500 ml and the reaction mixture is washed with 2×150 ml of ethyl acetate. The combined organic phases are washed with saturated sodium chloride solution, dried over sodium sulphate and evaporated. 20 g of the product with a purity of 93% are obtained. Ethyl 5-fluoro-1-methyl-3-difluoromethyl-1H-pyrazole-4-carboxylate in the form of a brown solid, which is reacted further without additional purification.

Example 3

5-Fluoro-1-methyl-3-difluoromethyl-1H-pyrazole-4-carbonyl chloride (I-1)

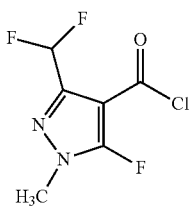

(I-1)

A solution of 22.3 g (100 mmol) of ethyl 5-fluoro-1-methyl-3-difluoromethyl-1H-pyrazole-4-carboxylate in 100 ml of toluene and 50 ml of 10% NaOH are stirred at AT for 3 hours. The aqueous phase is separated and adjusted to pH 5 with HCl. After extracting the product with chlorobenzene and azeotropically drying the organic phase, 23.8 g (200 mmol) of SOCl$_2$ are added to the solution and the mixture is heated at 80° C. for 2 hours. After evaporating the reaction mixture, 20.1 g of the product are obtained as an oil with a purity (GC) of 98%.

$^1$H NMR (CD$_3$CN): δ=6.88 (1H, t), 3.7 (3H, s) ppm.

Example 4

5-Fluoro-1-methyl-3-difluoromethyl-1H-pyrazole-4-carbonyl fluoride

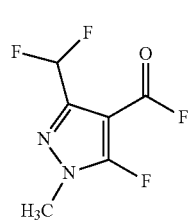

(I-2)

14.2 g (250 mmol) of spray-dried potassium fluoride, 22.8 g (100 mmol) of 5-chloro-1-methyl-3-difluoromethyl-1H-pyrazole-4-carbonyl chloride and 40 ml of sulpholane are heated to 155° C. with rapid stirring. The reaction is completed after 8 hours (GC monitoring). By distilling directly from the reaction mixture via a column under vacuum (1 mbar) at 100° C., 28 g of the product, which still contains approximately 20-30% of sulpholane, are obtained. A second distillation via a Vigreux column gives: 15.68 g of the product (80% yield) in the form of an oil.

GC/MS: m/z 196.

The invention claimed is:

1. A process for preparing a compound of formula (I)

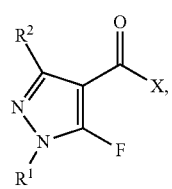

(I)

in which R$^1$ is C$_1$-C$_6$-alkyl, R$^2$ is C$_1$-C$_5$-fluoroalkyl and X is fluorine or chlorine, comprising the stages (1) chlorinating a compound of formula (II)

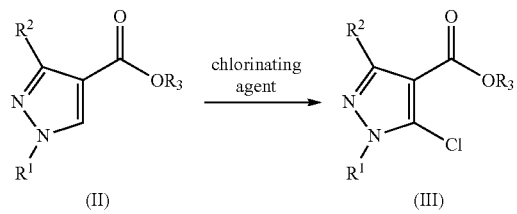

in which R$^1$ and R$^2$ have the meanings given above and R$^3$ is a linear or branched C$_{1-12}$-alkyl group, in the presence of a chlorinating agent to give a compound of formula (III), in which R$^1$, R$^2$ and R$^3$ have the meanings given above;

(2a-i) fluorinating the compound of formula (III) in the presence of a fluorinating agent of formula (IV), in which $M^+$ is $Li^+$, $Na^+$, $K^+$, $Cs^+$ or $Alk_4N^+$ and Alk is $C_1$-$C_4$-alkyl, to give a compound of formula (V);
(2a-ii) hydrolyzing a compound of the formula (V) to give a compound of formula (VIa); and
(2a-iii) subsequent halogenation to give the compound of the formula (I), in which X is fluorine or chlorine;

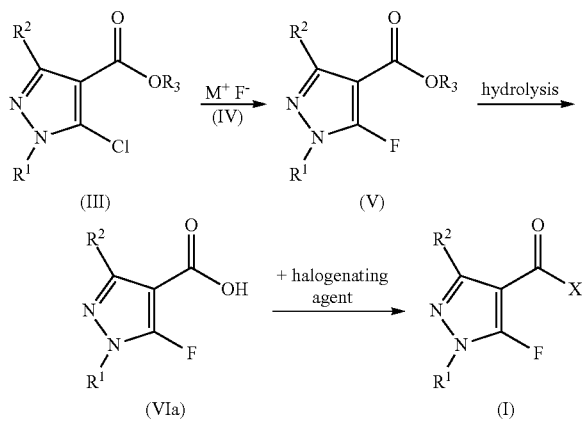

or
(2b-i) hydrolyzing a compound of formula (III) to give a compound of formula (VIb);
(2b-ii) subsequent halogenation of the a compound of formula (VIb) to give a compound of formula (VII); and

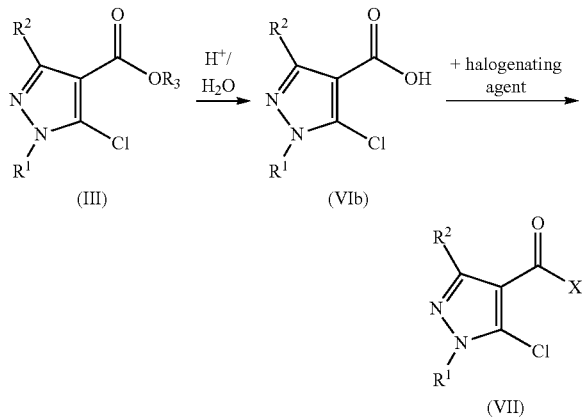

(2b-iii) fluorinating a compound of formula (VII) in the presence of a fluorinating agent of the formula (IV), to give a compound of formula (I), in which X is fluorine

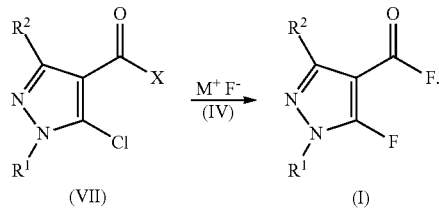

2. A process according to claim 1, wherein (2a) or (2b-ii) is carried out in the presence of a phase transfer catalyst.

3. A process according to claim 2, wherein the phase transfer catalyst is a quaternary ammonium salt, a salt of a phosphonium compound or an amidophosphonium salt.

4. A process according to claim 2, wherein the phase transfer catalyst is selected from the group consisting of tetramethylammonium chloride, tetramethylammonium bromide, tetrabutylammonium chloride, trimethylbenzylammonium chloride, tetrabutylammonium bromide, tetrabutylphosphonium chloride, tetrabutylphosphonium bromide, tetraphenylphosphonium chloride, tetraphenylphosphonium bromide, tetrakis(dimethylamino)phosphonium chloride, tetrakis(dimethylamino)phosphonium bromide, tetrakis(diethylamino)phosphonium chloride, tetrakis(diethylamino) phosphonium bromide, tris(diethylamino)(dimethylamino) phosphonium chloride, tris(diethyl-amino)(dimethylamino) phosphonium bromide, tris(dimethylamino)(dihexyl-amino) phosphonium chloride, tris(dimethylamino)(dihexylamino) phosphonium bromide, tris(diethylamino)(dihexylamino) phosphonium chloride, tris(diethylamino)(dihexylamino) phosphonium bromide, a hexaalkylguanidinium salt and polyethylene glycol dimethyl ethers with chain lengths r of 6 to 17 and an average molar mass of 500 g/mol.

5. A process according to claim 1, wherein the compound of formula (III) is ethyl 1-methyl-3-difluoromethyl-1H-pyrazole-4-carboxylate.

6. Ethyl 5-chloro- 1-methyl-3-difluoromethyl-1H-pyrazole-4-carboxylate.

7. Ethyl 5-fluoro- 1 -methyl-3-difluoromethyl-1H-pyrazole-4-carboxylate.

8. A process according to claim 2, wherein the compound of formula (III) is ethyl 1 -methyl-3 -difluoromethyl-1 H-pyrazole-4-carboxylate.

9. A process according to claim 3, wherein the compound of formula (III) is ethyl 1-methyl-3-difluoromethyl-1H-pyrazole-4-carboxylate.

10. A process according to claim 4, wherein the compound of formula (III) is ethyl 1-methyl-3-difluoromethyl-1H-pyrazole-4-carboxylate.

* * * * *